United States Patent
DiCarlo et al.

(10) Patent No.: US 7,618,362 B2
(45) Date of Patent: Nov. 17, 2009

(54) SPACER APPARATUS FOR RADIATION AND ABLATION THERAPY

(75) Inventors: Paul DiCarlo, Middleboro, MA (US); Robert F. Rioux, Ashland, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 231 days.

(21) Appl. No.: 11/090,144

(22) Filed: Mar. 28, 2005

(65) Prior Publication Data

US 2006/0217587 A1    Sep. 28, 2006

(51) Int. Cl.
*A61N 5/02* (2006.01)
(52) U.S. Cl. .......................................................... 600/2
(58) Field of Classification Search ............... 600/1–8; 604/21, 93.01; 607/116; 606/27; 623/1.12
See application file for complete search history.

(56) References Cited

U.S. PATENT DOCUMENTS

| | | |
|---|---|---|
| 5,213,561 A | 5/1993 | Weinstein et al. |
| 5,302,168 A | 4/1994 | Hess |
| 5,411,466 A | 5/1995 | Hess |
| 5,429,582 A | 7/1995 | Williams |
| 5,484,384 A | 1/1996 | Fearnot |
| 5,498,227 A | 3/1996 | Mawad |
| 5,611,767 A | 3/1997 | Williams |
| 5,643,171 A | 7/1997 | Bradshaw et al. |
| 5,840,008 A | 11/1998 | Klein et al. |
| 5,860,974 A | 1/1999 | Abele |
| 6,074,339 A | 6/2000 | Gambale et al. |
| 6,176,821 B1 | 1/2001 | Crocker et al. |
| 6,338,709 B1 | 1/2002 | Geoffrion et al. |
| 6,413,204 B1 | 7/2002 | Winkler et al. |
| 6,497,709 B1 | 12/2002 | Heath |
| 6,837,886 B2 | 1/2005 | Collins et al. |
| 2002/0035396 A1 | 3/2002 | Heath |
| 2002/0077520 A1 | 6/2002 | Segal et al. |
| 2003/0153802 A1 | 8/2003 | Bonan et al. |

*Primary Examiner*—Charles A Marmor, II
*Assistant Examiner*—Christine D Hopkins
(74) *Attorney, Agent, or Firm*—Cooley Godward Kronish LLP

(57) ABSTRACT

An apparatus comprises an elongated delivery member and a scaffold. The elongated delivery member has a distal end, a fixed portion and an actuator portion. The actuator portion is disposed proximate to the distal end. The actuator portion and the fixed portion are movable with respect to each other. The scaffold is mounted to the elongated delivery member proximate to the distal end. The scaffold has a first end coupled to the fixed portion. The scaffold has a second end coupled to the actuator portion. The scaffold is changeable between a stowed configuration and a deployed configuration by movement of at least the actuator portion and the fixed portion relative to each other.

21 Claims, 7 Drawing Sheets

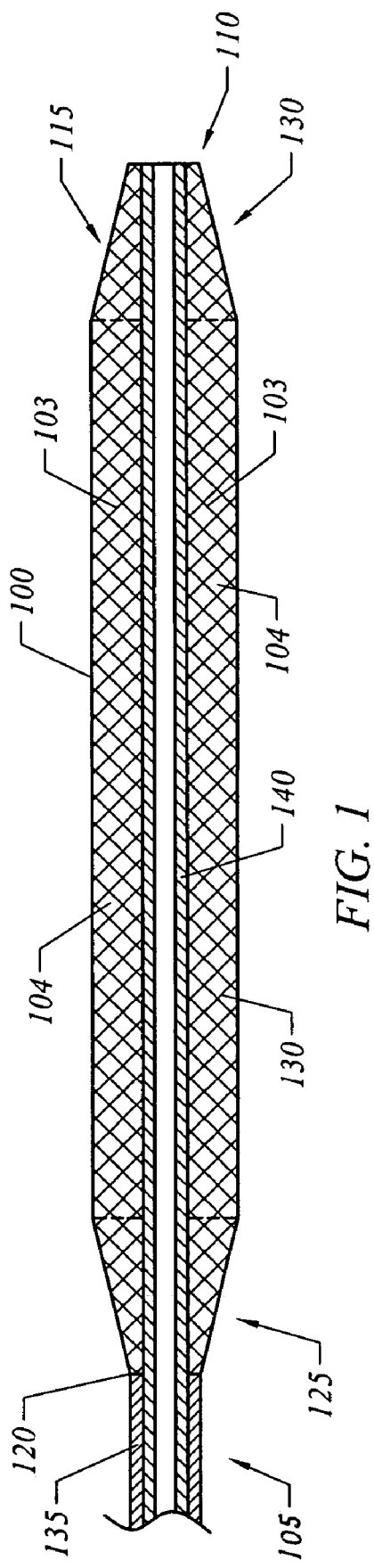
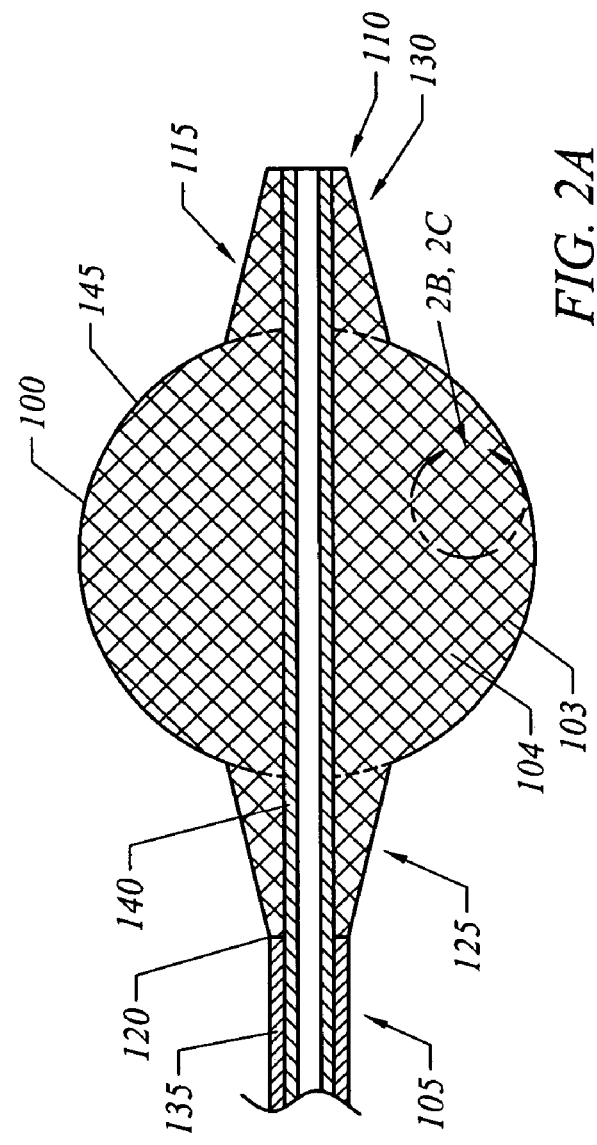
FIG. 1
FIG. 2A

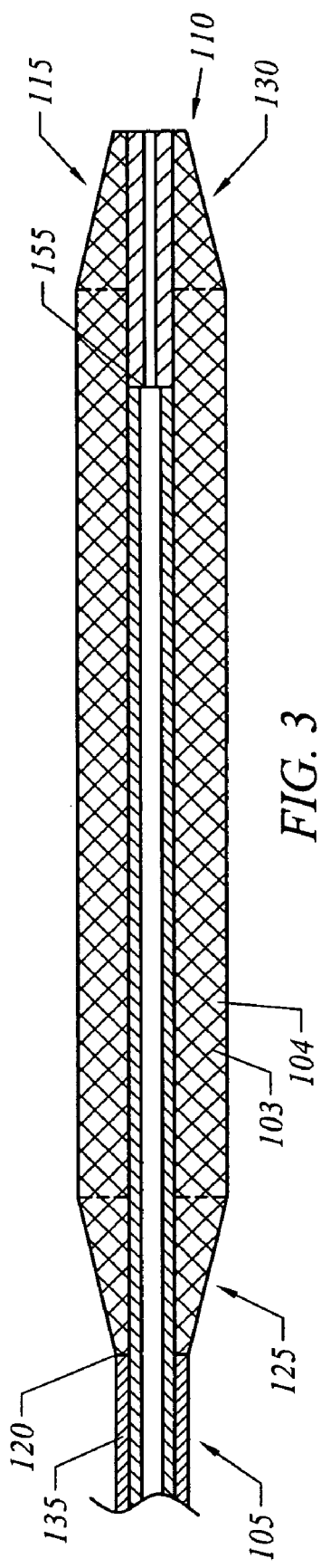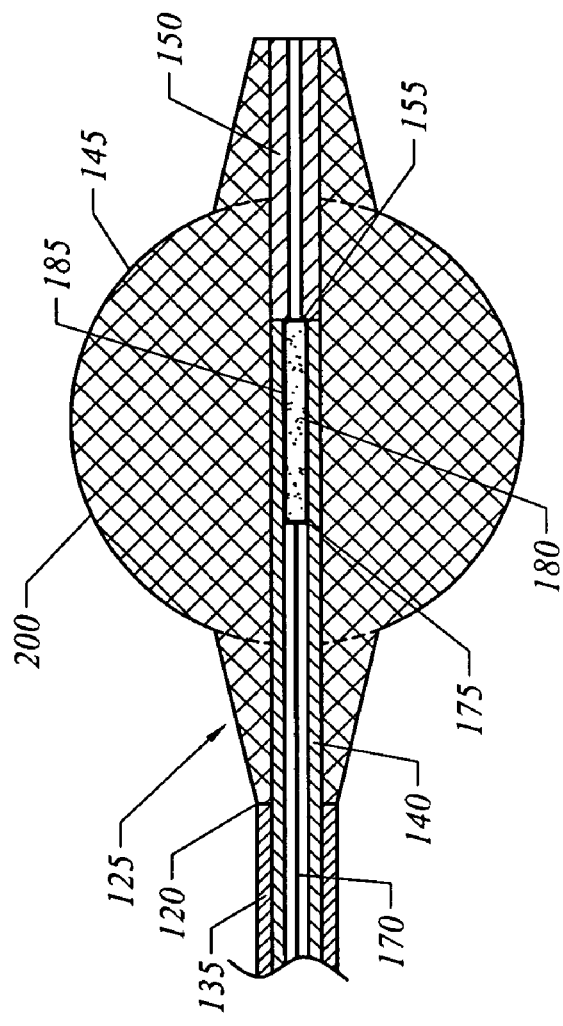
FIG. 3
FIG. 4

SPACER APPARATUS FOR RADIATION AND ABLATION THERAPY

BACKGROUND

The invention relates generally to apparatus for use in treating proliferative tissue disorders, and more particularly to an apparatus for the treatment of such disorders in the body by the application of radiation, RF energy and combinations thereof.

Malignant tumors are often treated by surgical resection of the tumor to remove as much of the tumor as possible. Infiltration of the tumor cells into normal tissue surrounding the tumor, however, can limit the therapeutic value of surgical resection because the infiltration can be difficult or impossible to treat surgically. Radiation therapy can be used to supplement surgical resection by targeting the residual tumor margin after resection, with the goal of reducing its size or stabilizing it. Radiation therapy can be administered through one of several methods, or a combination of methods, including permanent or temporary interstitial brachytherapy. The term "brachytherapy," as used herein refers to radiation therapy delivered by a spatially confined radioactive material inserted into the body at or near a tumor or other proliferative tissue disease site.

However, as is well known, the spacing between the radiotherapeutic source and the surrounding tissue is of interest because the radiation dose delivered by a radioactive source is inversely proportional to the square of the distance between the radiotherapeutic source and the tissue. Ideally, the radiotherapeutic source would be placed with respect to the tumor margin so that all of the margin receives the same dosage, i.e. that the tumor margin is disposed on an isodose surface generated by the radiotherapeutic source. A common geometry for an isodose surface would be a sphere. For a radiotherapeutic source with such an isodose surface geometry, the source would therefore be placed so that it is at the center of a sphere defined by the tumor margin. This would enable delivery of an effective tumor dose while minimizing damage to the surrounding normal tissue. This goal entails two requirements-matching the margin tissue geometry to the isodose surface geometry of the radiotherapeutic source and positioning the source accurately with respect to the margin tissue. The first requirement can be difficult to achieve when radiotherapeutic treatments are applied to soft tissue. Even if excision of the tumor produced a spherical post-surgical cavity, the soft tissue surrounding the cavity will have a tendency to slump, or deform. Portions of the unsupported soft tissue may deform towards or away from the radiotherapeutic source. Deviations of the tumor margin from the source's isodose surface will produce areas that are overdosed (and thus healthy tissue can suffer radionecrosis) and areas that are under dosed. Accordingly, improvements are needed not only to ensure the accurate placement of a radiotherapeutic source but also to maintain the tissue margin in a desired geometry during radiotherapy.

Situations arise where a surgeon may determine that a combination of radiotherapy and ablation treatment for a particular recision cavity is advisable. Because of the limitations of existing medical systems, this treatment regime may entail use of an ablation device followed by the use of a second different radiotherapy device. Accordingly, a need exists to provide a unitary treatment system capable of performing both radiotherapy and ablation treatment.

A need remains in radiotherapeutics for instruments providing more accurate radiotherapeutic source placement while improving support of the surrounding tissue. In addition, a need exists for such instruments that may also perform ablation treatments.

SUMMARY OF THE INVENTION

An apparatus comprises an elongated delivery member and a scaffold. The elongated delivery member has a distal end, a fixed portion and an actuator portion. The actuator portion is disposed proximate to the distal end. The actuator portion and the fixed portion are movable with respect to each other. The scaffold is mounted to the elongated delivery member proximate to the distal end. The scaffold has a first end coupled to the fixed portion. The scaffold has a second end coupled to the actuator portion. The scaffold is changeable between a stowed configuration and a deployed configuration by movement of at least the actuator portion and the fixed portion relative to each other.

BRIEF DESCRIPTION OF THE DRAWINGS

FIG. 1 is a cross-sectional view of an embodiment of a spacer apparatus according to the invention in a stowed configuration.

FIG. 2A is a cross-sectional view of the spacer apparatus of FIG. 1 in a deployed configuration.

FIG. 3 is a cross-sectional view of an alternative embodiment of a spacer apparatus in a stowed configuration and having a positioning feature according to the invention.

FIG. 4 is a cross-sectional view of the spacer apparatus of FIG. 3 in a deployed configuration and having a radiation source present within the apparatus.

DETAILED DESCRIPTION

Figure 2B:
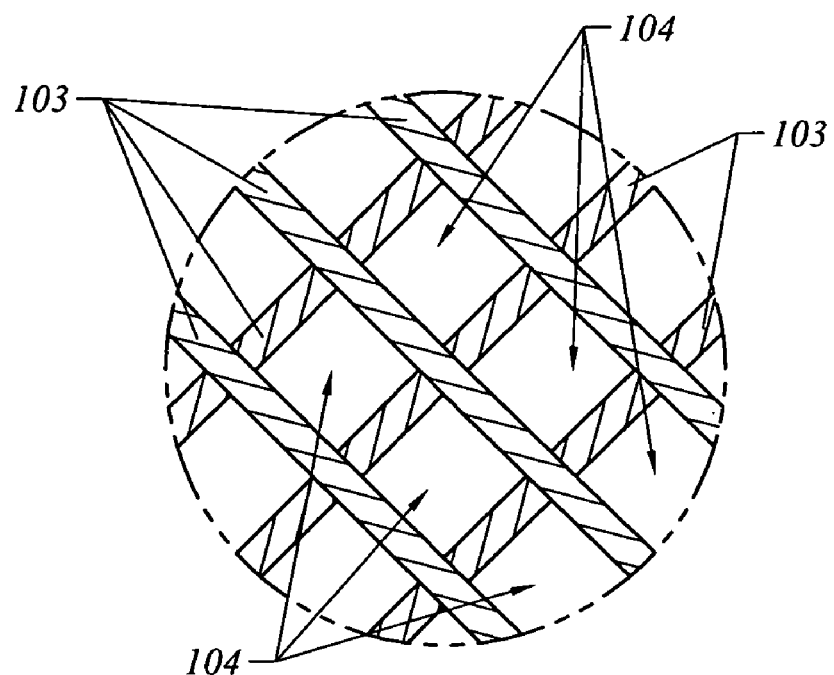
FIG. 2B is an enlarged view of the structural members of the spacer apparatus of FIG. 1.

The efficacy of brachytherapy improves when a physician is provided a definite operating envelope (i.e., a known geometry and location) in which to apply the desired radiotherapeutic treatment source. Accurate placement of the desired radiotherapeutic treatment source within a more definite operating envelope would further improve brachytherapy efficacy. Additionally, overall proliferative tissue treatment efficacy may be further improved through the advantageous combination of an RF ablation treatment and brachytherapy. These and other advantages are provided by embodiments of a spacer apparatus of the invention, as set forth below.

As used herein, a "scaffold" refers to a non-solid, reconfigurable structure of a predetermined shape for placement within a body cavity for deforming (or displacing) and supporting the tissue surrounding the body cavity approximately into the predetermined shape. The scaffold is non-solid because it includes multiple elongate, intersecting structural members and spaces or gaps defined by and between the elongate members. When used within body tissue, the scaffold supports the surrounding tissue directly and indirectly.

The scaffold directly supports the surrounding tissue where the tissue is in contact with at least one elongate member. Directly supported tissue assumes the overall shape of the scaffold. Indirect tissue support is provided to the surrounding tissue that is not in contact with an elongate member. Indirect support is provided by the scaffold as a function of the size of spaces or gaps between the elongate members. The scaffold provides indirect support by advantageously maintaining the spacing between the elongate members so that the tissue not in contact with an elongate member also remains at generally the same shape as the supported tissue (i.e., conforms generally to the overall shape of the scaffold). Indirect support and member spacing will vary as a function of the malleability of the surrounding tissue. Highly malleable tissue (i.e., soft tissue in a breast) may require smaller spaces between members to ensure that the indirectly supported soft tissue complies with the scaffold shape. If the scaffold is deployed into less malleable tissue, (i.e., tissue having less of a tendency to deflect into the spaces between elongate members) then larger spaces between members may be used. Through the advantageous use of both direct and indirect support, scaffolds described herein can increase the compliance of a variety of tissue types thereby ensuring the surrounding tissue conforms to the external shape of the scaffold. Increasing the compliance of the surrounding tissue to a definite geometry (i.e., the external shape of the scaffold) provides a more definite operating envelope within which a desired radiotherapeutic treatment can be provided.

As used herein, "cavity" refers to both naturally occurring and artificially created cavities within a body. Cavity is not limited to a specific geometry or location within the body. A naturally occurring cavity may exist, for example, within an organ such as the internal volume of the vagina, the bladder, the colon, the bile duct, the lungs, the eyes or the stomach. In addition, the definition of naturally occurring cavity includes lumens of the vasculature. Artificially created cavities are created through surgery such as tumor recision or other techniques to remove diseased tissue.

Figure 2C:
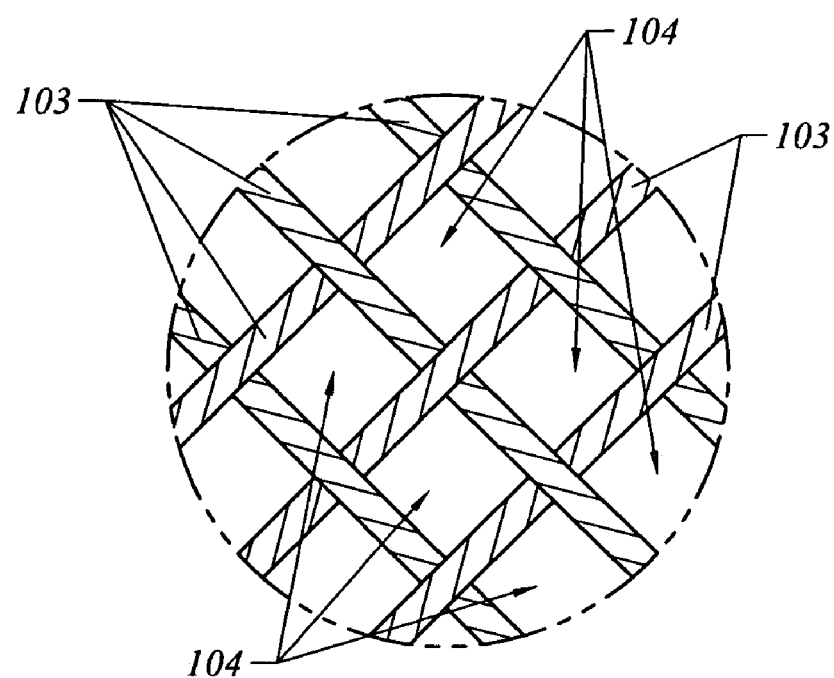
FIG. 2C is an enlarged view of an alternative embodiment of structural members of a spacer apparatus.

FIG. 1 illustrates a spacer apparatus including a scaffold 100 according to an embodiment of the invention. The scaffold 100 includes a plurality of intersecting structural members 103. Gaps or spaces 104 are formed by the intersecting structural members 103. The relationship between the intersecting members 103 and the spaces 104 is also shown in FIGS. 2A, 2B and 2C. FIG. 2B illustrates how the members 103 intersect in an overlapping pattern. FIG. 2C illustrates how members 103 intersect in a woven pattern. FIGS. 2B and 2C are only examples of intersection patterns used in scaffold embodiments of the invention. Other types of intersection patterns are possible. In some embodiments, gaps or spaces 104 are between about 0.5 mm² to about 20 mm².

The intersecting structural members 103 can be formed from any of a wide variety of metallic and/or non-metallic materials suited for use in biomedical applications. The material selected should have sufficient strength to deform (or displace) and then support (or retain) the surrounding tissue. The material selected should also have sufficient flexibility that it can elastically deform when the scaffold configuration changes from a stowed configuration to a deployed configuration. Suitable metallic materials can be, for example, formed a continuous solid mass of a highly elastic biocompatible metal such as a superelastic or pseudo-elastic metal alloy, for example, a nitinol (e.g., 55% nickel, 45% titanium). Other examples of superelastic materials include, e.g., Silver-Cadmium (Ag—Cd), Gold-Cadmium (Au—Cd), Gold-Copper-Zino (Au—Cu—Zn), Copper-Aluminum-Nickel (Cu—Al—Ni), Copper-Gold-Zinc (Cu—Au—Zn), Copper-Zinc (Cu—Zn), Copper-Zinc-aluminum (Cu—Zn—Al), Copper-Zinc-Tin (Cu—Zn—Sn), Copper-Zinc-Xenon (Cu—Zn—Xe), Iron Beryllium ($Fe_3Be$), Iron Platinum ($Fe_3Pt$), Indium-Thallium (In—Tl), iron-manganese (Fe—Mn) Nickel-Titanium-Vanadium (Ni—Ti—V), Iron-Nickel-Titanium-Cobalt (Fe—Ni—Ti—Co) and Copper-Tin (Cu—Sn). See Schetsky, L. McDonald, "Shape Memory Alloys", *Encyclopedia of Chemical Technology* ($3^{rd}$ ed.), John Wiley & Sons, 1982, vol. 20. pp. 726-736 for a full discussion of superelastic alloys. Other examples of metals suitable for the scaffold include stainless steel, titanium and various alloys of these metals and the precursor of superelastic alloys. Precursors of superelastic alloys are those alloys that have the same chemical constituents as superelastic alloys, but have not been processed to impart the superelastic property. Suitable non-metallic materials can include, for example, shape memory polymers (SMP) including polyethylene and other biocompatible plastics. Suitable shape memory polymers may be selected from the four classes of SMP described by Liu et al in "Tailored Shape Memory Polymers: Not all SMPs are Created Equal" (2002), which is incorporated herein by reference in its entirety. The Four SMP classes described by Liu are (1) the chemically cross-linked glassy thermo sets; (2) the chemically cross-linked semi-crystalline rubbers; (3) the physically cross linked thermo plastics and (4) the physically cross linked block copolymers. In other embodiments, the scaffold may be formed from combinations of metallic and non-metallic materials described above.

Returning to FIG. 1, the scaffold 100 is connected to an elongated delivery member 105. The elongated delivery member 105 has a distal end 110, a fixed portion 120 and an actuator portion 115. The actuator portion 115 is disposed proximate to the distal end 110. The actuator portion 115 and/or the fixed portion 120 is moveable with respect to each other. The scaffold 100 is mounted to the delivery member 105 proximate to the distal end 110. The scaffold 100 has a first end 125 coupled to the fixed portion 120 and a second end 130 coupled to the actuator portion 115.

The elongated delivery member 105 can be any of a wide variety of structures suited to deploying medical implements. In the illustrated embodiment, the elongated delivery member 105 includes a first tube 135 and a second tube 140 where the second tube 140 (also referred to as the "inner tube") is disposed within the first tube 135 (also referred to as the "outer tube"). The first tube 135 includes the fixed portion 120 and the second tube 140 includes the actuator portion 115. While the illustrative embodiments of FIGS. 1 and 2A illustrate the relationships described above, other configurations are possible. For example, the first tube may be disposed within the second tube. The first and second tubes may be, for example, concentrically arranged catheters.

The scaffold 100 is shown in a stowed configuration. The scaffold is changeable between a stowed configuration (FIG. 1) and a deployed configuration (FIG. 2A) by movement of the actuator portion 115 and/or the fixed portion 120 with respect to each other. The actuator portion 110 is suitably connected (i.e., within the elongated delivery member 105) to a conventional handle assembly (not shown) that allows a user to move the actuator portion 115 relative to the fixed portion 120. In other words, by pushing the outer tube 135 towards the actuator portion 115 of the inner tube 140 while the position of the actuator portion 115 is substantially maintained, the fixed portion 120 of the outer tube 135 moves toward the actuator portion 115 of the inner tube 140, thereby deploying the scaffold 100. Alternatively, by pulling the inner tube 140 away from the fixed portion 120 of the outer tube 135 while the position of the fixed portion 120 is substantially maintained, the actuator portion 115 of the inner 140 moves toward the fixed portion 120, thereby deploying the scaffold 100. When in the deployed configuration (FIG. 2A), the scaffold exterior surface 145 is an approximately spherical shape.

While in the illustrative embodiments of FIGS. 1 and 2A the fixed portion 120 is located proximally to the actuator portion 115, other configurations are possible. For example, in another representative embodiment, the fixed portion 120 can be located distally to the actuator portion 115. In this representative embodiment, the scaffold 100 moves from a stowed configuration to a deployed configuration when the actuator portion 115 is moved distally towards the fixed portion 120.

Note that the depictions in the figures including FIG. 1 are not necessarily drawn to scale. In some cases, such depictions are drawn in an exaggerated manner for illustrated purposes. For example, the actuator portion 115 in FIG. 1 is drawn in an exaggerated manner for illustrated purposes. In some embodiments, the actuator portion is much smaller relative to the other portions of the scaffold.

The scaffold 100 is moveable between a stowed configuration (FIG. 1) and a deployed configuration (FIG. 2A). The reduced profile of the stowed configuration is particularly useful for delivery and positioning of the scaffold 100 to a target site inside the patient. In radiotherapy applications, the target site is for example a recision cavity. Once in position within the recision cavity, the scaffold is expanded into the deployed configuration causing the tissue surrounding the recision cavity to take the appropriate shape, by conforming to the scaffold outer surface 145. The volume of the deployed scaffold is considered to be the interior portion of the scaffold within the outer surface 145. The deployed scaffold volume will generally correspond to the approximate amount of tissue resected, or be slightly larger. If a slightly larger deployed scaffold volume is used, then the larger volume outer surface of the scaffold is used to more forcibly urge the tissue on the surface of the resected region into the scaffold shape.

Forcible compliance of the surrounding tissue to the scaffold shape may, when the scaffold embodiment is used as a brachytherapy spacer, promote more even dose distribution around the outer spatial volume in the target tissue. Accordingly, in some embodiments, the external shape of the scaffold 100 in a deployed configuration (FIG. 2A) is selected to deform the surrounding tissue into an arrangement that is conducive to effective radiotherapy. When used in an interstitial brachytherapy application, the scaffold outer surface 145 should establish a relationship between a radioactive source within the scaffold and the target tissue so as to achieve the desired dosing profile. The optimal shape of the scaffold is therefore a function of the shape and type of radiotherapeutic material selected. If the type of radiotherapeutic material selected emits radiation at a high dose rate, then a larger volume scaffold may be selected. If the type of radiotherapeutic material selected emits radiation at a low dose rate, then smaller volume scaffold may be selected. If a solid, spherically shaped radiotherapeutic is selected, then a scaffold that deforms the surrounding tissue into a generally spherical shape is desired. As used herein, the term "generally spherical shape" refers to an exterior scaffold shape that is conducive to effective radiotherapy using spherically shaped radiotherapeutics disposed within the interior of the scaffold 100.

In some scaffold embodiments, a material covering is placed around the scaffold to further improve the conformity of the surrounding tissue to the scaffold size and shape. The use of a material covering augments the direct and indirect support features of the scaffold by covering the gaps or spaces between the elongated members. The material covering may be woven or knitted so as to be expandable as the scaffold moves between stored and deployed configurations. In addition, the cover material should be water permeable, have a low radioactive shielding value (i.e., the material has a clinically negligible impact on the efficacy of radiotherapy applications) and has negligible electrical insulation properties. Possible covering materials are, for example, Dacron, polyester, and biocompatible materials such as vascular graft materials. In one embodiment, the deployed scaffold has a generally spherical shape with a largest diameter of 1 cm to 7 cm. The material covering may be positioned and suitably affixed to the exterior scaffold surface or the interior scaffold surface. One advantage of positioning the material covering on the interior scaffold surface is that such a position is less likely to interfere with or complicate the operation of ablation capable scaffold embodiments such as scaffolds 300, 400 of FIGS. 5 and 6.

While useful for purposes of discussion, it is not essential that the scaffold 100 have a generally spherical shape when in a deployed configuration. For example, when a scaffold embodiment is used as a spacer for brachytherapy, the scaffold outer surface 145 can correspond to the desired dosing profile. Other scaffold shapes can be created to correspond with other types and shapes of radiotherapeutic materials. In other words the absorbed dose within the target tissue at points equidistant from the scaffold outer surface 145 can be substantially uniform in substantially every direction. Put another way, the three dimensional dosing profiles generated by a radiation source within the scaffold can be substantially similar in shape to the scaffold outer surface 145. For example, a scaffold can be configured to conform the surrounding tissue for treatment using a dosing profile generated by a cylindrically shaped radiation source. Additionally, other scaffold embodiments can also be shaped to accommodate other than solid radiotherapeutic materials (i.e., gels or liquids). Other embodiments are possible where different dosing profiles such as isodose or non-isodose are used and one or both of the cavity shape and the scaffold shape is something other than spherical or cylindrical shapes discussed above.

The illustrated embodiment of the scaffold 100 in FIG. 2A has a generally spherical shape in the deployed configuration. Alternatively, other embodiments of the scaffold can provide a deployed scaffold volume and diameter that is variable and adjustable based upon the amount of relative movement between the first and second ends of the scaffold 125, 130. As such, the scaffold may be connected to the delivery member such that a user may deflect the first and second ends of the scaffold (125, 130) to expand the scaffold 100 into the desired shape and/or size. Thus, relative movement between the first and second delivery members (i.e., tubes 135, 140) may be used to adjust the volume and/or diameter of the deployed scaffold. According to this embodiment, a user can use a single, adjustable scaffold that is expandable anywhere within a range of volumes and/or diameters corresponding to a range of recision cavity sizes.

In one alternative scaffold embodiment the size of the deployed scaffold is selectable and includes a locking means to fix the scaffold into the selected size. For example, consider a scaffold having a deployed configuration diameters ranging from 0.5 cm. to 8 cm. Scaffold markings can be provided in a suitable location, such that a user may know the scaffold size as the scaffold is positioned into a deployed configuration. For example, in some embodiments, the first delivery member 135 and/or the second delivery member 140 has ruled markings to indicate the extent to which the delivery member(s) has been displaced, thereby indicating the deployed size of the scaffold. Alternatively, the first delivery member 135 can cooperate with the second delivery member 140 to provide a series of detents indicating the deployed size of the scaffold.

Corresponding to the markings, locking features are provided so that the scaffold may be fixed into a desired deployment size. The operation of the locking means will vary depending upon the configuration of the scaffold, the attachment between the scaffold and the actuator portion, and movement needed for scaffold appointment. Any of a variety of locking means may be used that allow the scaffold to be locked into a desired size and then later unlocked and changed to a stowed configuration or locked into a different size. One advantage of the locking means aspect of this embodiment of the invention is that the markings allow a user to know with greater certainty the size of the deployed scaffold. Knowledge of the size of the deployed scaffold helps ensure that an appropriate scaffold size is used within the estimated recision cavity size. Another advantage of the locking means is that the locking means may also be used to reinforce the scaffold shape in support of the surrounding tissue as the surrounding tissue is urged into conformity with the deployed scaffold size and shape.

It may be desirable, particularly when working with soft tissue, to have the scaffold expand into a volume somewhat larger than the actual recision cavity. Thus, brachytherapy procedures, for example, may be simplified by the fact that only one adjustable scaffold is needed during the procedure. The physician (i.e., user) may estimate the size of the recision cavity and then select and deploy an appropriately sized scaffold into the cavity. In one embodiment, the deployed scaffold has a generally spherical shape with a diameter of 1 cm to 7 cm. In another embodiment, the deployed scaffold has a generally spherical shape with a diameter of 2 cm to 6 cm.

In another alternative embodiment, a scaffold is sized and constructed to have only have a single fixed volume when deployed rather than having an adjustable deployed volume. In this embodiment, a brachytherapy procedure, for example, may be simplified because the user will be presented scaffolds of various sizes from which to select. The user need only select the scaffold of appropriate size, depending upon the size of the recision cavity. A locking means, as described above, may also be used with these embodiments to hold the scaffold into the deployed configuration.

Returning to the embodiment shown in FIGS. 1 and 2A, the spacer apparatus includes a scaffold 100 having a stowed configuration (FIG. 1) and a deployed configuration (FIG. 2A). The scaffold 100 is attached to the first and the second delivery members whereby relative movement between the first and the second delivery members (i.e., tubes 135 and 140) moves the scaffold from the stowed configuration to the deployed configuration. Referring to FIG. 1, the first delivery member may be the first tube 135 that is attached to the scaffold 100 at the first end of the scaffold 125. The second delivery member may be the second tube 140 that is attached to the scaffold 100 at the distal end 110. The second tube 140 is slideable with respect to the first tube 135 such that when moving from the stowed configuration to the deployed configuration the second end of the scaffold 110 moves towards the first end of the scaffold 125.

In an alternative embodiment shown in FIGS. 3 and 4, the spacer apparatus includes a radiation source locating feature 150. The radiation source locating feature 150 is disposed within the interior volume of scaffold 200 (which is similar to the embodiments of the scaffold 100 described above but for the addition of radiation source locating feature 150). Scaffold 200 also has a stowed configuration (FIG. 3) and a deployed configuration (FIG. 4). Movement of the scaffold 200 from the stowed configuration to the deployed configuration, or a variety of variable volume deployed configurations, is accomplished using the techniques described above with regard to scaffold 100.

The radiation source locating feature 150 is advantageously positioned to optimize the location of a radioactive source 180 disposed within and relative to the scaffold 200. The radiation source locating feature 150 is disposed within scaffold 200 such that when scaffold 200 is in the deployed configuration a radiation source 180 disposed adjacent the radiation source locating feature 150 will be located to effectively expose the tissue adjacent the scaffold to the therapeutic rays of the radiation source 180. As shown in FIG. 4, radiation source locating feature 150 is positioned so that a radiation source 180, or as illustrated, a radiation source 180 disposed in or held by a radiation source holder 185, disposed into contact with feature 150 will be generally centrally located within the deployed configuration volume of an embodiment of scaffold 200. A radiation source delivery member 170 is connected to radiation source holder 185; radiation source 180 is disposed within or coupled to the holder 185.

In other embodiments, the radiation source locating feature is disposed to improve radiotherapy treatment efficacy. For example, the radiation source locating feature proximate end 155 can be disposed within the scaffold 200 such that when a radiation source 180 or source holder 185 is placed against the feature, the radiation source 180 or source holder 185 will be located to expose the tissue adjacent the scaffold 200 to the therapeutic rays of the radiation source 180. The radiation source locating feature may therefore be located in a variety of positions and locations depending upon, for example, the specific radiation source, source holder, cavity geometry, and desired dosage. In the embodiment illustrated in FIG. 4, the radiation source locating feature proximate end 155 is positioned so that a radiation source holder 185 placed into contact with it can be positioned to effectively treat the tissue surrounding the scaffold 200.

In the illustrative embodiments of FIGS. 3 and 4, radiation source locating feature 150 is disposed at the distal end of the second tube 140 and connected to the delivery member distal end 110. In this embodiment, the radiation source locating feature 150 is an additional tube with a thicker inner wall sized so that a radioactive source 180 or source holder 185 traveling along the interior of the second tube 140 will come into contact with and be stopped by the radiation source locating feature proximate end 155. In the illustrative embodiments of FIGS. 3 and 4, the radiation source locating feature 150 is an appropriately sized additional tube having a thicker inner wall. It is to be appreciated that a number of other mechanical structures could also act as a radiation source locating feature 150. For example, the radiation source locating feature can be a pin or other solid blockage positioned transverse to the deployment pathway of the radiation source. The radiation source locating feature 150 position could also be adjusted for cooperative use with the earlier described variable size scaffold. Stops (not shown) could be inserted into the interior of the second tube 140 against the feature 150 to adjust the location of the radioactive source holder 185 within the scaffold 200. Through the use of stops or other insertable structures the feature 150 may be modified to correspond to a desired location for each of the different scaffold sizes.

The radiation source locating feature 150 may be formed from a suitable material to increase its visibility to medical imaging systems. For example, the radiation source locating feature 150 may be formed from a radiopaque material to allow the use of a fluoroscope for positioning. Alternatively, the radiation source locating feature 150 may be formed of a material and have a suitably shaped exterior surface to ensure that it is more easily located using an ultrasound imaging system.

In another embodiment, the radiation source locating feature 150 is a feature that is tactilely perceptible to the person placing the radiation source 180 or source holder 185 within the scaffold 200. For example, the radiation source locating feature 150 could be any structure that resists the movement of the radiation source 180 or source holder 185. This structure would translate into the sensation of resistance or other perceptible tactile sensation indicating the end of further distal movement of radiation source 180 or source holder 185 within the scaffold 200. In another example, the radiation source locating feature 150 could be a structure, notch, groove or slot positioned within the scaffold 200 configured to engage with a protrusion or other suitable feature positioned on the radiation source 180 or source holder 185. The engagement of the protrusion or other suitable feature with the notch, groove or slot within the scaffold 200 is perceptible by a user, or by a device under control of a user when urging the radiation source 180 or source holder 185 into position within the scaffold 200. Moreover, the tactile feature is cooperatively used with a suitable visual marker to indicate scaffold size. Thus, a user moving the scaffold from one deployed position to another would see the visual marker and be able to perceive or feel the scaffold locking into each of the various sizes until the desired size is obtained.

In yet other embodiments where the size of the scaffold is adjustable, the radiation source locating feature can be used in conjunction with mechanisms for determining the deployed size of the scaffold. For example, in embodiments where the deployed size of the scaffold can be determined by the ruled markings on the first and/or second delivery member, the radiation source locating feature can be incorporated into the radiation source delivery member 170. For example, the radiation source delivery member can have a selectable position stop so that the radioactive source holder 185 or the radiation source 180 is positioned at a desired location within the scaffold. In an alternative embodiment, a radiation source delivery member of a desired length can be selected from a set of radiation source delivery members after the deployed size of the scaffold has been determined.

The radiation source 180 may be any of a wide variety of materials containing a predetermined radionuclide that emits radiation, such as radionuclides that emit photons (e.g., gamma radiation) or particles (such as beta particles), or other therapeutic rays. Alternatively, the radiation source may be any radionuclide that emits energy sufficient to damage the DNA of cells in a portion of the tissue adjacent the expanded structure. The radiation source 180 may be a material that contains, for example, $I^{125}$, $I^{131}$, $Yb^{169}$, $Pd^{132}$, $Xe^{124}$, $Ba^{130}$, iridium or other sources of radiation. Other solid radionuclides that could be used as a radioactive source 180 are currently generally available as brachytherapy radiation sources. Additionally, the source holder 185 could be appropriately selected to allow the use of non-solid radioactive sources such as radioactive liquids or gels. The radiation source holder 185 is shaped and sized according to the selected radiation source 180. The radiation source holder 185 may be formed from any material that provides structural support for the radiation source 180 and serves as the attachment point to the radiation source delivery member distal end 175. The radiation source delivery member distal end 175 may include structure or features to cooperatively engage with structures or features on the radiation source holder 185. The use of cooperative features for attaching the radiation source delivery member distal end 175 to the radiation source holder 185 provides for ease of use and allows the radiation source to be more easily adapted to a variety of radiation source holders. In this manner, the radiation source delivery member 170 may be used with a wider variety of radiation source holders 185 and radioactive sources 180. The radiation source holder 185 may also be designed to hold the radioactive source 180 and provide shielding designed to tailor the radiotherapy being applied. For example, the radiation source holder 185 may be formed from material having variable transmissivity or be a non-uniform shield material. Aligning a high transmissivity portion of the holder towards the desired radiotherapy treatment area (i.e., low shielding area of the holder) and maintaining low transmissivity portions towards the healthy tissue (i.e., high shielding area of the holder) will help improve the efficacy of the radiotherapy by more precise source placement and also protect the healthy tissue adjacent the cavity by providing additional shielding.

The radiation source delivery member 170, radiation source holder 185 and radiation source 180 are illustrated within scaffold 200 in the deployed configuration (FIG. 4) for purposes of illustration and discussion. The radiation source delivery member 170, radiation source holder 185 and radiation source 180 may also be present when scaffold 200 is in the stowed configuration (FIG. 3). Moreover, in scaffold embodiments adapted for RF ablation (i.e., monopolar RF ablation scaffolds 300 and/or bipolar RF ablation scaffolds 400, discussed below), the radiation source delivery member 170, the radiation source holder 185 and the radiation source 180 may also be present within the scaffold embodiment during the ablation treatment.

In one embodiment, there is provided an apparatus for treating tissue adjacent an expanded structure located within a cavity in a body. The apparatus includes an elongated delivery member and an expanded structure attached to the elongated delivery member. In addition, a radiation source locating feature is provided within the expanded structure. The radiation source locating feature is disposed within the expanded structure whereby a radiation source delivered along or through the elongated delivery member and brought into contact with the radiation source locating feature is positioned in a desired location within the expanded structure. In one embodiment, the desired location is generally centrally located within the expanded structure. In another embodiment, the desired location is within the expanded structure to dispose a radiation source for delivery of radiation therapy to tissue surrounding the expanded structure.

Figure 5:
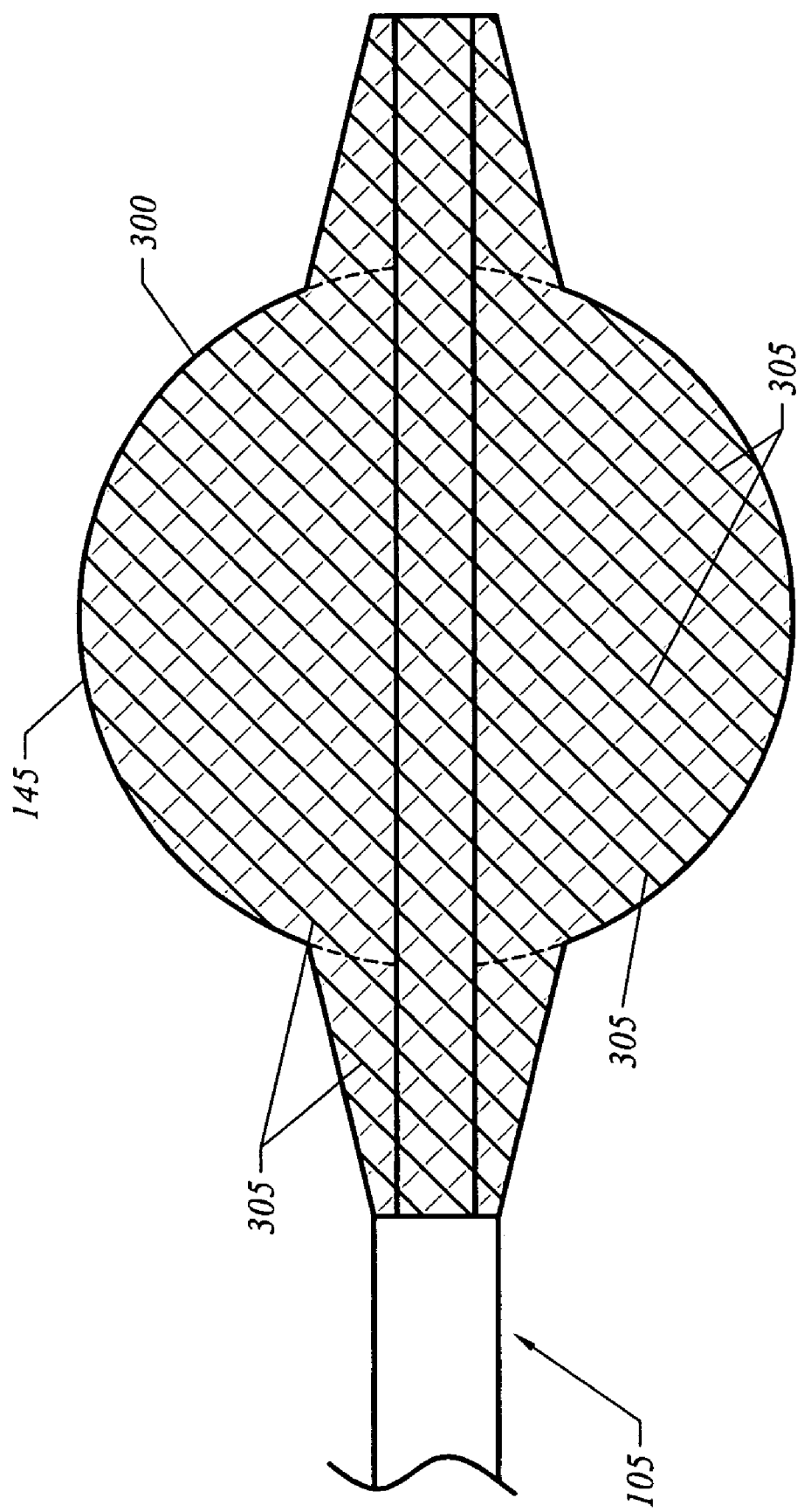
FIG. 5 is a side view of an embodiment of a spacer apparatus adapted for ablation treatment.
Figure 6:
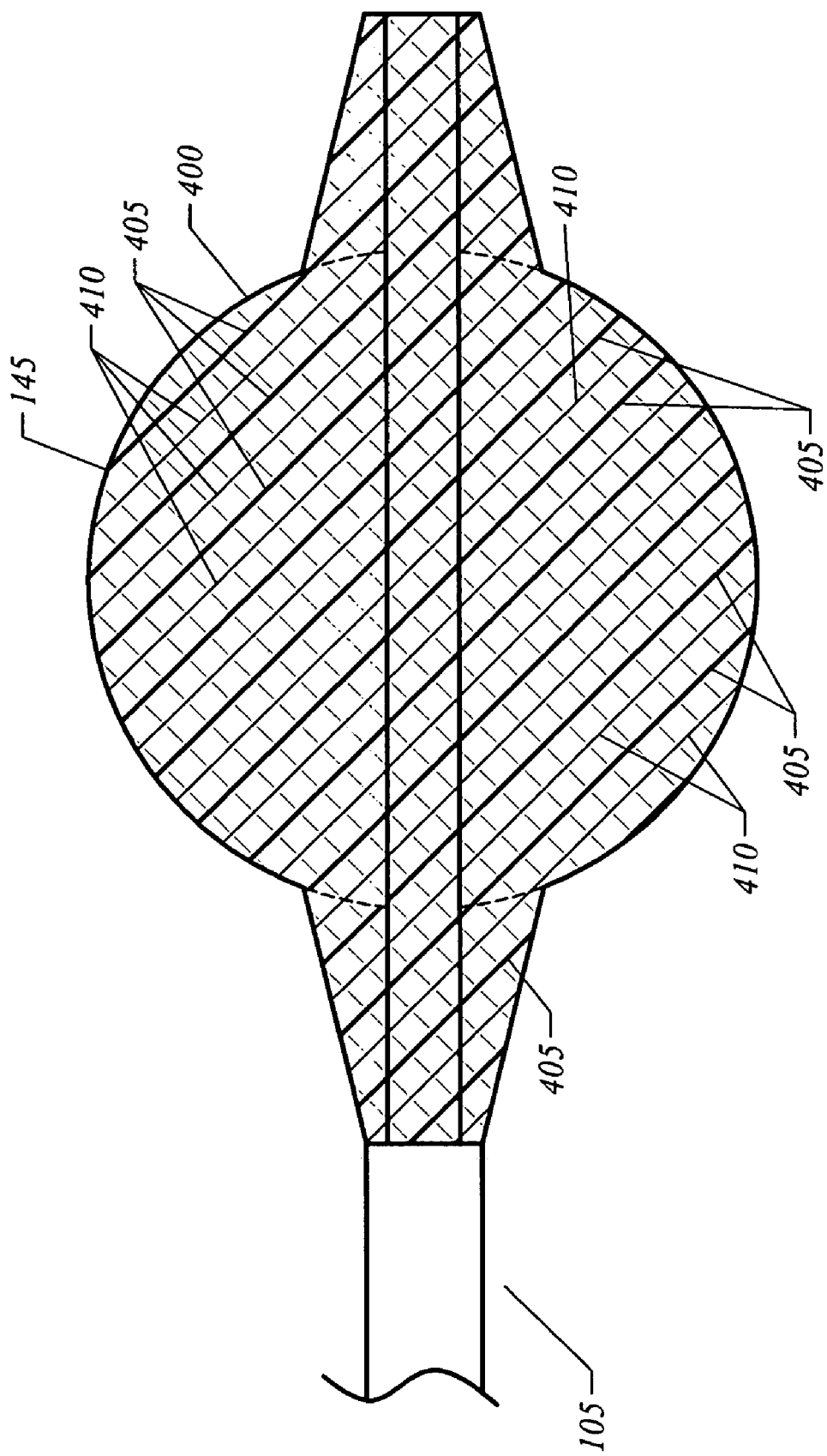
FIG. 6 is a side view of another embodiment of a spacer apparatus adapted for ablation treatment.

Additional spacer apparatus embodiments include scaffolds 300, 400 adapted for use as RF ablation treatment instruments (FIGS. 5 and 6). In scaffold embodiments adapted for RF ablation treatment, a select portion or all of the scaffold is electrically conductive and/or inductive. The scaffold is electrically connected to a known electrical power source and RF control unit such that the scaffold operates as an ablation device or as an ablation electrode. In one embodiment, the scaffold 300 operates as a monopolar RF ablation scaffold. In another embodiment, the scaffold 400 operates as a bipolar RF ablation scaffold. In one illustrative embodiment, for example, the elongate members 103 of the scaffold 300, 400 may be metallic. In another illustrative embodiment, all or a select portion of the scaffold 300, 400 structural members are either formed from an electrically conductive or inductive material or are coated with an electrically inductive or conductive material.

Scaffolds 300, 400 adapted for ablation treatments are similar to and may include the functionalities and/or characteristics of the scaffolds 100, 200 embodiments described above, such as direct and indirect support of surrounding tissue, adjustable and/or fixed size, composition, variable shapes and deployment techniques. In addition, when an embodiment of a scaffold 300 or 400 is in a deployed configuration, the scaffold 300, 400 also presses against the surrounding tissue sufficiently to make effective electrical contact. As such, deployed configurations exist for monopolar ablation scaffolds 300 and bipolar ablation scaffolds 400 that increase the efficacy of a desired ablation therapy.

A combination of radiotherapy and ablation treatment may be desirable in some circumstances. Combining the radiation therapy and ablation treatment into a single instrument may simplify the post tumor recision procedures, help ensure the target tissue receives both ablation and radiotherapy and reduce the number of instruments used to perform the procedures. Accordingly, a need exists to provide a unitary treatment system capable of performing thermal ablation therapy before a radiotherapy treatment. Embodiments of ablation scaffolds 300,400 may be advantageously used as such unitary treatment instruments for combination therapies. One advantage of these embodiments is that they enable more precise placement of the radiotherapeutic source within the patient, improve support of tissue surrounding the therapeutic source and provide a single instrument capable of both radiotherapy and ablation treatment.

In operation an ablation scaffold (i.e., a scaffold 300 or 400) is disposed in a cavity and then deployed into a configuration suited to the desired ablation therapy. In some cases, expanding the scaffold into substantially complete contact with the surrounding tissue is a configuration suited to ablation therapy. The same scaffold, in the same position, may then be used for the desired radiotherapeutic treatment by disposing a radioactive source within the scaffold. In addition, the scaffold 300, 400 embodiments may include suitable radioactive source location features embodiments described above to position the radioactive source is positioned in the desired location within the scaffold. Thereafter, the radioactive source and scaffold may remain within a patient for some desired period of time. Subsequent ablation treatments may also be performed in conjunction with additional radiotherapies. The amount of ablation therapy and radiotherapeutic dose applied may vary overtime as desired.

The variable configuration capabilities of the scaffold may also be used to advantage when a desired ablation scaffold configuration differs from a desired radiotherapy scaffold configuration. For example, an ablation scaffold (i.e., a scaffold 300 or 400) is deployed into a first configuration selected to increase the efficacy of the desired ablation therapy. Then, the same scaffold is adjusted into a second, different, deployed configuration. In this case the second, different deployed configuration is selected to increase the efficacy of a desired radiotherapeutic treatment. To further increase the efficacy of a desired radiotherapeutic treatment, these scaffold embodiments may include embodiments of the radioactive source location feature described above selected, modified, or otherwise adapted for use with a specific radiotherapeutic source or holder.

Ablation scaffolds 300, 400 may be configured as part of either a monopolar ablation system in the case of scaffolds 300 or a bipolar ablation system in the case of scaffolds 400 or a hybrid ablation scaffold having both monopolar and bipolar characteristics. Accordingly, known electrical power supplies (not shown), RF control systems (not shown) and connections (not shown) to the electrically conductive portions of the scaffold 300 are provided to configure the scaffold 300 as a monopolar ablation device. Likewise, known electrical power supplies (not shown), RF control systems (not shown) and connections (not shown) to the electrically conductive portions of the scaffold 400 are provided to configure the scaffold 400 as a bipolar ablation device. As used herein, "conductive portions" means any material suited to receive electrical energy, either by conduction, induction or combinations thereof. Likewise, "conducted" is not limited to transmission of electrical energy by conduction but also includes induction and combinations thereof. Ablation therapy encompasses a wide variety of treatments where energy is applied to tissue. The amount of energy applied to the tissue includes sufficient energy to warm the tissue to sufficient energy to disrupt the cellular structure of the tissue or irreparably damage the tissue. In an application where raising tissue temperature is the desired ablation therapy, the tissue temperature may be elevated, for example, between 50° C. to 100° C. In another application where raising tissue temperature is desired non-ablation therapy, the tissue temperature may be elevated, for example, to 41° C.

Turning now to FIG. 5, which shows in one illustrative monopolar ablation system, the conductive portions (darker members 305 as shown in FIG. 5) of the scaffold 300 would act as one electrode. Current is applied to the conductive portions 305 of the scaffold 300 using suitable known electrical connections and control methods. The current is conducted through the tissue to another electrode in the form of a ground plate that has a surface area many times that of the electrode portion of the scaffold 300. As is the conventional practice, this ground plate is maintained in contact with the skin of the patient. Because of the large size of the ground plate, when the current reaches it, the density is so low that no burning or heating occurs, as is well known. A typical embodiment is where the scaffold is one electrode and the second electrode is located elsewhere on the delivery member, e.g., at the atraumatic tip or at another portion of the scaffold.

Embodiments of the scaffold 400 may be advantageously constructed and configured as bipolar ablation devices. (FIG. 6). In the bipolar ablation configuration, a first conductive portion 405 forms the first electrode. A second conductive portion 410, suitably electrically isolated from the first electrode or first conductive portion 405, forms the second electrode. During bipolar operation, the RF current flows through the tissue between the first and second electrodes.

Embodiments of the ablation scaffolds 300 and 400, that include the features described above for embodiments of scaffolds 100 and 200, provide the added advantage of being unitary instruments for performing both ablation and brachytherapy. One embodiment of such an apparatus for delivering radioactive emissions and RF energy to an internal body location would include an elongated delivery member and an expandable structure attached to the elongated delivery member. The expandable structure defines a spatial volume selected to be conducive to brachytherapy and also forms the electrode of an ablation device. Alternatively, a portion of the expanded structure forms an electrode of a tissue ablation system. Additionally, there is also provided a holder for a source of radioactive emissions disposed nearly centrally to the spatial volume defined by the expandable structure. There may be a source of radioactive emissions disposed in the holder. The source of radioactive emissions is a radionuclide that emits photons, beta particles, gamma radiation, or other therapeutic rays. In some embodiments, the source of radioactive emissions is a solid.

Figure 7:
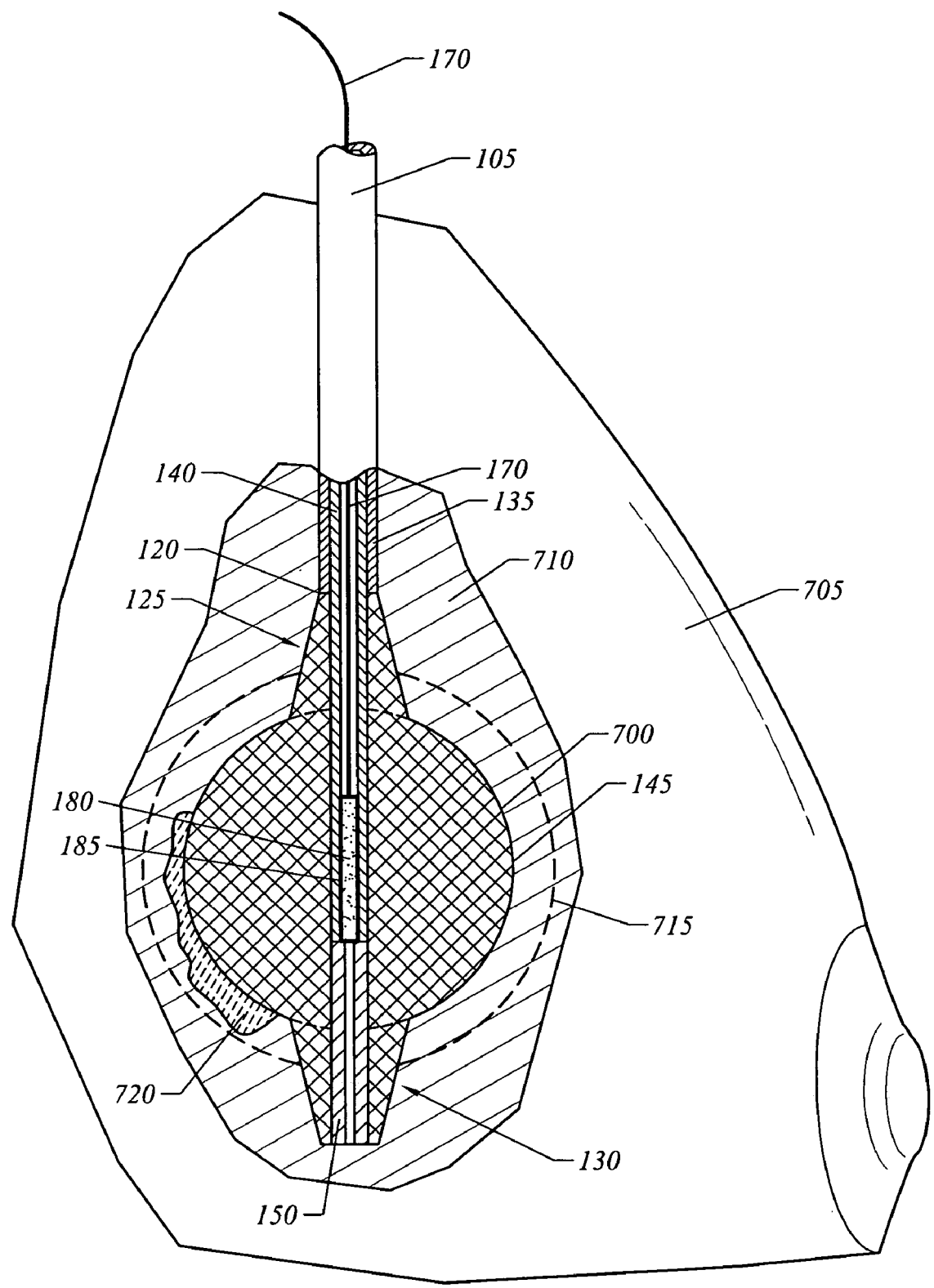
FIG. 7 is a cross-sectional view of an embodiment of a spacer apparatus deployed within a recision cavity in a breast.

FIG. 7 illustrates a scaffold 700 in a deployed configuration within a recision cavity formed in the soft tissue 710 of a breast 705. As will be further detailed in the description that follows, embodiments of the scaffold 700 may be similar to and include the functionalities and/or characteristics of the scaffold embodiments 100, 200, 300 and 400 described above, such as direct and indirect support of surrounding tissue, adjustable and/or fixed size, composition, variable shapes, and RF ablation types. As described above with regard to other scaffold embodiments, the scaffold 700 is placed into the recision in a stowed configuration. Similar to scaffold 100, as the scaffold 700 moves into the deployed configuration, the scaffold 700 has sufficient strength to contact and then deform surrounding soft tissue 710 into conformity with the shape of the scaffold surface 145. The spaces or gaps defined by and between the elongate members have been selected so that the soft tissue 710 surrounding the recision is supported (directly and/or indirectly) and thereby generally conforms to the shape of the deployed scaffold. Radiation source holder 185 is positioned against the positioning feature 150 so that the source 180 is generally centrally located within the volume of the scaffold 700 and hence the surrounding tissue 710. The radioactive source 180 has a generally spherical radiodose profile illustrated as the kill zone 715. The kill zone 715 indicates that portion of the tissue surrounding radioactive source 180 where cells are killed and/or or cell DNA is destroyed. Scaffold 700 and positioning feature 150 have been advantageously configured such that the kill zone 715 includes the remaining cancerous tissue 720 that is the target of the treatment.

Scaffold 700 is also in sufficient contact with surrounding tissue 710 to enable operation as an ablation device (i.e., such as ablation scaffolds 300, 400). As such, FIG. 7 illustrates a spacer apparatus configured to advantageously support and shape a recision cavity into a definite desired shape, position a radiotherapeutic source within that shaped cavity into a position complementing the isodose profile of the radiotherapeutic source, and provide an ablation instrument for ablation treatment of the surrounding tissue. In one embodiment, the ablation treatment can be performed before positioning the radiotherapeutic source within the cavity.

While illustrated in a recision cavity in a breast 705, the scaffold 700, as well as the other scaffold embodiments described above, may be sized for use in any surgically formed cavity, cavity formed by tumor removal or in any other body cavity as well. For example, some scaffold embodiments may be used where a tumor was removed from a breast, a lung or a bile duct. Alternatively, some scaffold embodiments may be advantageously employed where the cavity is a naturally occurring body cavity such as, for example, the vagina, the lungs, the uterus, the bile duct or the bladder of a body.

Figure 8:
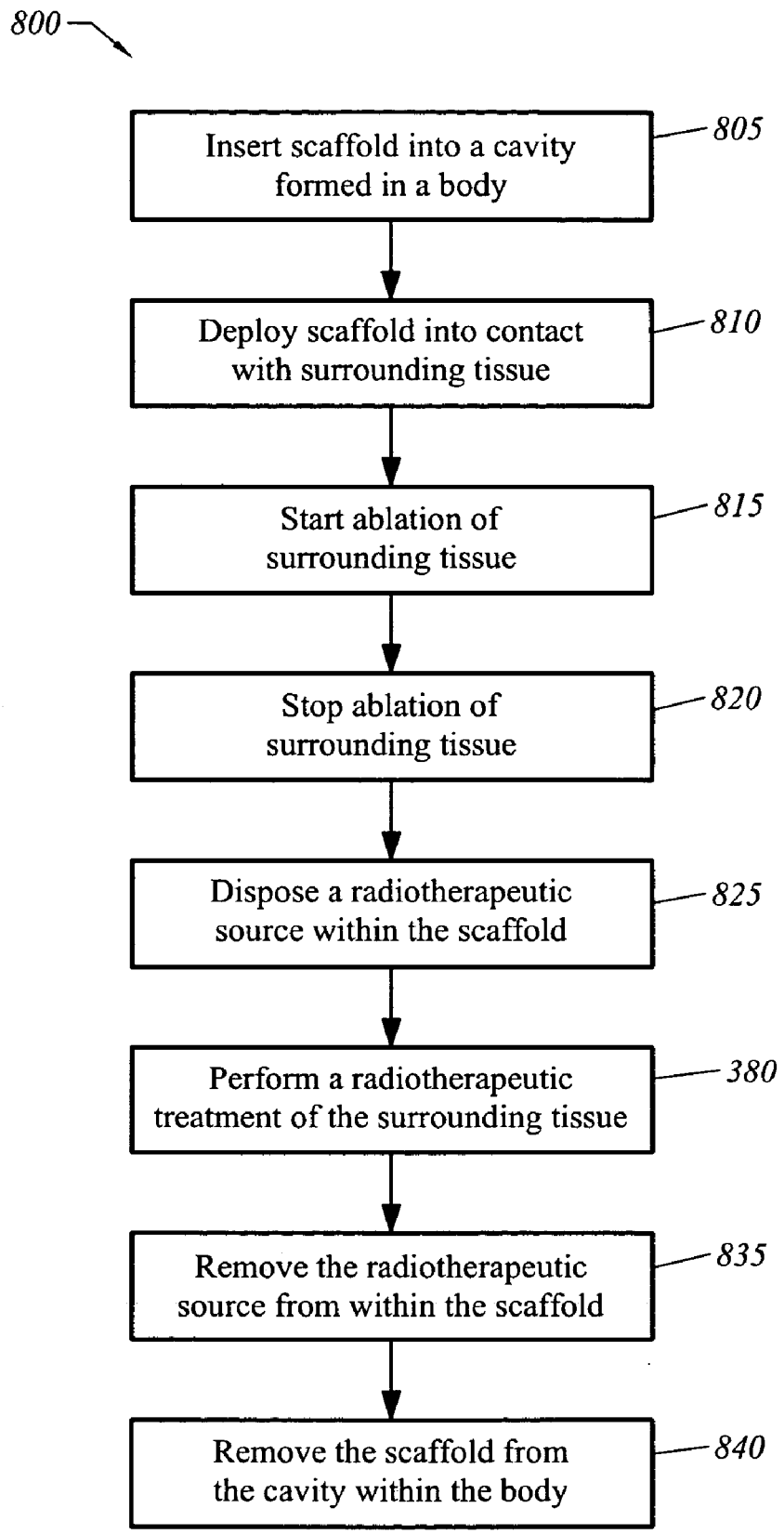
FIG. 8 is a flow chart of an embodiment of a combined ablation and brachytherapy treatment method.

Embodiments of the invention also provide methods for performing ablation and/or radiotherapy treatments in a body. One illustrative embodiment is set forth in flowchart 800 (FIG. 8). First, insert the scaffold into a cavity formed in a body (step 805). Next, deploy the scaffold into contact with the surrounding tissue (step 810). Start the ablation treatment of the surrounding tissue (step 815). After passage of the desired amount of time, stop the ablation treatment (step 820). Next, dispose a radiotherapeutic source within the scaffold (step 825). Perform a radiotherapeutic treatment of the surrounding tissue by keeping the radiotherapeutic source in the scaffold for the desired time period (step 830). When the desired time period for radiotherapy has elapsed, remove the radiotherapeutic source from within the scaffold (step 835). Finally, remove the scaffold from the cavity within the body (step 840).

The steps described above for flowchart 800 are merely illustrative of one embodiment of the methods of the present invention. Modifications to the above method are possible. In another embodiment, for example, the steps relating to the radiotherapeutic treatment (825, 830, and 835) may be performed before the steps relating to the ablation treatment (815 and 820). In yet another embodiment, the steps relating to the radiotherapeutic treatment (825, 830, and 835) may be performed concurrent with or otherwise overlap in time the steps relating to the ablation treatment (815 and 820). Other embodiments include earlier described scaffold alternatives. Consider, for example, an embodiment where the ablation treatment is performed with a scaffold adapted for ablation therapies, and the radiotherapeutic treatment is performed using a scaffold adapted for the radiotherapy treatments. In this example, the ablation scaffold will be inserted into the body cavity and remains present during the ablation treatment. The ablation scaffold will then be removed from the body cavity. Next, the radiotherapeutic scaffold will be inserted into the body cavity and remain during the radiotherapeutic treatment. When the radiotherapeutic treatment ends, the radiotherapeutic scaffold is removed. Another alternative embodiment of this illustrative example includes using the radiotherapeutic scaffold, and performing the radiotherapeutic treatment before the ablation treatment.

Other modifications of the method embodiments are possible. Another embodiment provides a method for treating a post operative cavity in a body that includes inserting an electrically conductive scaffold into the post operative cavity and expanding the scaffold into a generally spherical shape. Expanding the scaffold conforms the cavity into a shape that generally conforms to the shape of the expanded scaffold. A portion of the tissue proximate to the post operative cavity is ablated by applying electrical power to the scaffold. A portion of the tissue proximate to the post operative cavity is irradiated by positioning a radioactive source in about the center of the generally spherical shape of the scaffold. In one embodiment, the apparatus used to for ablation of the tissue is present in the cavity when the surrounding tissue is irradiated. In another alternative embodiment, the apparatus used for irradiating the surrounding tissue is present during the ablation treatment of the surrounding tissue. In yet another alterative embodiment, a single apparatus is used for both the ablation treatment and the irradiation treatment.

Still other method embodiments are possible. Another embodiment is a method for radiation treatment to tissue surrounding a cavity in a body using a scaffold having an expanded shape conducive to brachytherapy. In one embodiment, the method includes inserting the scaffold into a cavity formed in a body and expanding the scaffold into an expanded shape that is conducive to effective radiotherapy. The expanded shape conducive to effective radiotherapy may be, in some specific embodiments, a generally spherical shape. The scaffold in its expanded shape comes into contact with and deforms the tissue surrounding the cavity generally into the expanded shape of the scaffold. Additionally, the scaffold in its expanded shape may be attached proximally and distally to an elongated delivery member. Expanding the shape and deforming the tissue surrounding the cavity may be caused by relative movement between the distal and proximal attachment points. Additionally, a source of radiotherapeutic material may be positioned within the expanded shape to provide the desired radiotherapy dosage to the tissue surrounding the cavity. In addition, a radioactive source positioning feature may be provided and used to position the radioactive source within the scaffold.

Another method embodiment provides for treating a post operative cavity in a body using a scaffold attached proximally and distally to an elongated delivery member. There is also provided a radioactive source positioning feature on the elongated delivery member. The scaffold is inserted into the post operative cavity. The scaffold is expanded into a generally spherical shape through relative motion between the proximal attachment point in the distal attachment point. The expanded scaffold deforms the tissue surrounding the cavity generally into the shape of the expanded scaffold. A radioactive source is positioned in contact with the positioning feature thereby irradiating a portion of the tissue proximate to the post operative cavity. In an alternative embodiment, at least a portion of the scaffold forms an electrode for an ablation device. Further to this alternative embodiment, a portion of the tissue proximate to the scaffold is ablated by applying electrical power to the scaffold. Some embodiments of the inventive method provide for the use of a single scaffold for performing both ablation and radiotherapy, other embodiments of the inventive method provide for the use of a first scaffold optimized for ablation treatment and a second scaffold optimized for radiotherapy treatments. In one such embodiment, a first scaffold is used to perform an ablation treatment in the body cavity. After the ablation treatment, the first scaffold is removed from the body cavity and a second different scaffold is inserted into the body cavity. After the second scaffold is deployed into the body cavity, a radiotherapeutic treatment of the surrounding tissue is performed by disposing a radiotherapeutic source within the second scaffold.

While various embodiments of the invention have been described above, it should be understood that they have been presented by way of example only, and not limitation. Thus, the breadth and scope of the invention should not be limited by any of the above-described embodiment examples, but should be defined only in accordance with the following claims and their equivalents.

While the invention has been particularly shown and described with reference to embodiments thereof, it will be understood by those skilled in the art that various changes in form and details may be made therein without departing from the spirit and scope of the invention.

What is claimed is:

1. An apparatus for delivering radioactive emissions and RF energy to an internal body location, comprising:
    an elongated delivery member including a distal end, a fixed portion and an actuator portion, the actuator portion of the elongated delivery member being disposed proximate to the distal end of the elongated delivery member, the actuator portion of the elongated delivery member and the fixed portion of the elongated delivery member being moveable with respect to each other;
    an expandable structure attached to the elongated delivery member, the expandable structure having a first end and a second end, the expandable structure is mounted proximate to the distal end of the elongated delivery member, the first end of the expandable structure being coupled to the fixed portion of the elongated delivery member, the second end of the expandable structure being coupled to the actuator portion of the elongated delivery member, the expandable structure being changeable between a stowed configuration and a deployed configuration by movement of at least the actuator portion and the fixed portion relative to each other, the expandable structure defining a spatial volume that is approximately spherical when in the deployed configuration and forming an electrode of an ablation device; and
    a holder for a source of radioactive emissions that is approximately centrally and internally disposed within the spatial volume defined by the expandable structure when in the deployed configuration.

2. The apparatus of claim 1, further comprising a source of radioactive emissions disposed in the holder.

3. The apparatus of claim 1, further comprising a source of radioactive emissions disposed in the holder, the source of radioactive emissions being a radionuclide that emits at least one of photons or energetic particles.

4. The apparatus of claim 1, further comprising a source of radioactive emissions disposed in the holder, the source of radioactive emissions being a solid.

5. The apparatus of claim 1, wherein the expandable structure is a scaffold.

6. The apparatus of claim 1, wherein the expandable structure is a scaffold configured so that altering the scaffold from the stowed configuration to the deployed configuration deforms the surrounding soft tissue into conformity with a shape of the scaffold.

7. The apparatus of claim 1, wherein the holder is disposed within the spatial volume such that an amount of radioactive emissions is substantially equal at a margin tissue when the expandable structure contacts the margin tissue and when the expandable structure is in the deployed configuration.

8. The apparatus of claim 1, wherein the holder is disposed within the spatial volume such that the holder is substantially equidistant from a margin tissue when the expandable structure contacts the margin tissue and when the expandable structure is in the deployed configuration.

9. An apparatus, comprising:
    an elongated delivery member including a distal end, a fixed portion and an actuator portion, the actuator portion of the elongated delivery member being disposed proximate to the distal end of the elongated delivery member, the actuator portion of the elongated delivery member and the fixed portion of the elongated delivery member being moveable with respect to each other;
    an expandable structure coupled to the elongated delivery member, the expandable structure having a first end and a second end, the expandable structure is mounted proximate to the distal end of the elongated delivery member, the first end of the expandable structure being coupled to the fixed portion of the elongated delivery member, the second end of the expandable structure being coupled to the actuator portion of the elongated delivery member, the expandable structure being changeable between a stowed configuration and a deployed configuration by movement of at least the actuator portion and the fixed portion relative to each other;
    a radiation source locating feature; and
    a radiation source, the elongated delivery member defining a range of motion of the radiation source including an end location, the end location corresponding to the radiation source being in contact with the radiation-source-locating feature and within the expandable structure when in the deployed configuration, the end location of the elongated delivery member is approximately centrally and internally disposed within the expandable structure when in the deployed configuration.

10. The apparatus of claim 9, wherein the end location of the elongated delivery member is a location within the expandable structure when in the deployed configuration such that the radiation source is configured to deliver radiation therapy to tissue surrounding the expandable structure when in the deployed configuration.

11. The apparatus of claim 9, wherein a portion of the expandable structure forms an ablation electrode.

12. The apparatus of claim 9, wherein the radiation source is a radionuclide that emits energy sufficient to damage the DNA of cells in a portion of the tissue adjacent the expandable structure when in the deployed configuration.

13. The apparatus of claim 9, the deployed configuration is a first deployed configuration, wherein:
the expandable structure is changeable between the stowed configuration, the first deployed configuration and a second deployed configuration, a size of the first deployed configuration being different from a size of the second deployed configuration.

14. The apparatus of claim 9, further comprising:
a radiation source delivery member configured to couple to a radiation source, the radiation source delivery member being slideably moveable with respect to the elongated delivery member, at least one of the elongated delivery member and the radiation source delivery member having a radiation source locating feature.

15. The apparatus of claim 9, wherein the radiation source is configured such that an amount of radiation by the radiation source is substantially equal at a margin tissue when the expandable structure contacts the margin tissue and when the expandable structure is in the deployed configuration and the radiation source is in contact with the radiation-source-location feature.

16. The apparatus of claim 9, wherein the radiation source is configured such that the radiation source is substantially equidistant from a margin tissue when the expandable structure contacts the margin tissue and when the expandable structure is in the deployed configuration and the radiation source is in contact with the radiation source-location-feature.

17. The apparatus of claim 9, wherein the expandable structure is a scaffold.

18. The apparatus of claim 9, wherein the expandable structure is a scaffold configured so that altering the scaffold from the stowed configuration to the deployed configuration deforms the surrounding soft tissue into conformity with a shape of the scaffold.

19. An apparatus, comprising:
an elongated delivery member including a distal end, a fixed portion and an actuator portion, the actuator portion of the elongated delivery member being disposed proximate to the distal end of the elongated delivery member, the actuator portion of the elongated delivery member and the fixed portion of the elongated delivery member being moveable with respect to each other;

an expandable structure attached to the elongated delivery member, the expandable structure having a first end and a second end, the expandable structure is mounted proximate to the distal end of the elongated delivery member, the first end of the expandable structure being coupled to the fixed portion of the elongated delivery member, the second end of the expandable structure being coupled to the actuator portion of the elongated delivery member, the expandable structure being changeable between a stowed configuration and a deployed configuration by movement of at least the actuator portion and the fixed portion relative to each other, the expandable structure defining an approximately spherical volume when in the deployed configuration and forming an electrode of an ablation device; and a holder for a source of radioactive emissions that is entirely disposed within the elongated delivery member, a location of the holder within the elongated delivery member being internal within the approximately spherical volume defined by the expandable structure when in the deployed configuration and substantially corresponding to a center of the approximately spherical volume defined by the expandable structure when in the deployed configuration.

20. The apparatus of claim 19, wherein the expandable structure is a scaffold.

21. The apparatus of claim 19, wherein the expandable structure is a scaffold configured so that altering the scaffold from the stowed configuration to the deployed configuration deforms the surrounding soft tissue into conformity with a shape of the scaffold.

* * * * *